US007778707B2

(12) United States Patent
Shuros et al.

(10) Patent No.: US 7,778,707 B2
(45) Date of Patent: Aug. 17, 2010

(54) METHOD AND DEVICE FOR MYOCARDIAL STRESS REDISTRIBUTION

(75) Inventors: Allan C. Shuros, St. Paul, MN (US);
Rodney W. Salo, Fridley, MN (US);
Shantha Arcot-Krishnamurthy, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 343 days.

(21) Appl. No.: 11/689,032

(22) Filed: Mar. 21, 2007

(65) Prior Publication Data

US 2008/0234772 A1    Sep. 25, 2008

(51) Int. Cl.
*A61N 1/368* (2006.01)
(52) U.S. Cl. .......................................... 607/11; 607/15
(58) Field of Classification Search .................... 607/15, 607/11
See application file for complete search history.

(56) References Cited

U.S. PATENT DOCUMENTS

| 6,128,535 | A  | * | 10/2000 | Maarse .......................... 607/28 |
| 6,292,693 | B1 | * | 9/2001  | Darvish et al. .................. 607/9 |
| 6,725,093 | B1 | * | 4/2004  | Ben-Haim et al. ............. 607/9 |
| 6,965,797 | B2 | * | 11/2005 | Pastore et al. .................. 607/17 |
| 7,277,761 | B2 |   | 10/2007 | Shelchuk |

FOREIGN PATENT DOCUMENTS

WO    WO 98/10831    *    3/1998

OTHER PUBLICATIONS

Adamopoulos, S., "Effects of pulsed beta-stimulant therapy on beta-adrenoceptors and chronotropic responsiveness in chronic heart failure.", *Lancet*, 345(8946), (Feb. 11, 1995), 344-9.
Butler, C. K., et al., "Cardiac responses to electrical stimulation of discrete loci in canine atrial and ventricular ganglionated plexi", *Am J Physiol.*, 259(5 Pt 2), (Nov. 1990), H1365-73.
Coats, A. J., "Controlled trial of physical training in chronic heart failure. Exercise performance, hemodynamics, ventilation, and autonomic function.", *Circulation*, 85(6), (Jun. 1992), 2119-31.
Koizumi, T., "Improvement of left ventricular dysfunction during exercise by walking in patients with successful percutaneous coronary intervention for acute myocardial infarction.", *Circ J.*, 67(3), (Mar. 2003), 233-7.

(Continued)

*Primary Examiner*—Scott M Getzow
*Assistant Examiner*—Michael Kahelin
(74) *Attorney, Agent, or Firm*—Schwegman, Lundberg & Woessner, P.A.

(57) ABSTRACT

Methods and devices are described for delivering electrical stimulation to the heart in a manner that advantageously redistributes myocardial stress during systole for therapeutic purposes in the treatment of, for example, post-MI and HF patients. Pre-excitation pacing may be applied to deliberately de-stress a particular myocardial region that may be expected to undergo deleterious remodeling, such as the area around a myocardial infarct or a hypertrophying region or to deliberately stress a region remote from the pre-excitation pacing site in order to exert a cardioprotective conditioning effect, similar to the beneficial effects of exercise. Pre-excitation pacing may be advantageously combined with inotropic electrical stimulation applied to the stressed region.

20 Claims, 4 Drawing Sheets

OTHER PUBLICATIONS

Leier, C. V., "Drug-induced conditioning in congestive heart failure.", *Circulation*, 65(7), (Jun. 1982), 1382-7.

Liang, C., "Conditioning effects of chronic infusions of dobutamine. Comparison with exercise training.", *Journal of Clinical Investigation*, 64(2), (Aug. 1979), 613-9.

Myers, J., "Exercise training and myocardial remodeling in patients with reduced ventricular function: one-year follow-up with magnetic resonance imaging", *Am Heart J.*, 139(2), (Feb. 2000), 252-61.

Wolfel, E. E., "Marathoners or couch potatoes: what is the role of exercise in the management of heart failure?", *Current Heart Failure Reports*, 2(1), (Mar. 2005), 25-34.

* cited by examiner

METHOD AND DEVICE FOR MYOCARDIAL STRESS REDISTRIBUTION

RELATED CASES

This application is related to U.S. patent application Ser. No. 11/427,517, filed on Jun. 29, 2006 and Ser. No. 11/561,049, filed on Nov. 17, 2006, which are hereby incorporated by reference in their entirety.

FIELD OF THE INVENTION

This invention pertains to cardiac rhythm management devices such as pacemakers and other implantable devices.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Ventricular remodeling leads to further dysfunction by decreasing the compliance of the ventricles (thereby increasing diastolic filling pressure to result in even more congestion) and causing eventual wall thinning that causes further deterioration in cardiac function. It has been shown that the extent of ventricular remodeling is positively correlated with increased mortality in HF patients.

A myocardial infarction (MI) is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm, where all of the muscle fibers in the area are destroyed and replaced by fibrous scar tissue. Even if the ventricular dysfunction as a result of the infarct is not immediately life-threatening, a common sequela of a transmural myocardial infarction, or any major MI, especially in the left ventricle, is heart failure brought about by ventricular remodeling in response to the hemodynamic effects of the infarct that causes changes in the shape and size of the ventricle. The remodeling is initiated in response to a redistribution of cardiac stress and strain caused by the impairment of contractile function in the infarcted area as well as in nearby and/or interspersed viable myocardial tissue with lessened contractility due to the infarct. Following an MI, the infarcted area includes tissue undergoing ischemic necrosis and is surrounded by normal myocardium. Until scar tissue forms and even after it forms, the area around the infarcted area is particularly vulnerable to the distending forces within the ventricle and undergoes expansion over a period of hours to days. Over the next few days and months after scar tissue has formed, global remodeling and chamber enlargement occur due to complex alterations in the architecture of the ventricle involving both infarcted and non-infarcted areas. It has been found that the extent of left ventricular remodeling in the late period after an infarction, as represented by measurements of end-systolic and end-diastolic left ventricular volumes, is an even more powerful predictor of subsequent mortality than the extent of coronary artery disease.

Remodeling is thought to be the result of a complex interplay of hemodynamic, neural, and hormonal factors that occur primarily in response to myocardial wall stress. As noted above, one physiological compensatory mechanism that acts to increase cardiac output is increased diastolic filling pressure of the ventricles as an increased volume of blood is left in the lungs and venous system, thus increasing preload. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction.

DETAILED DESCRIPTION

Figure 1:
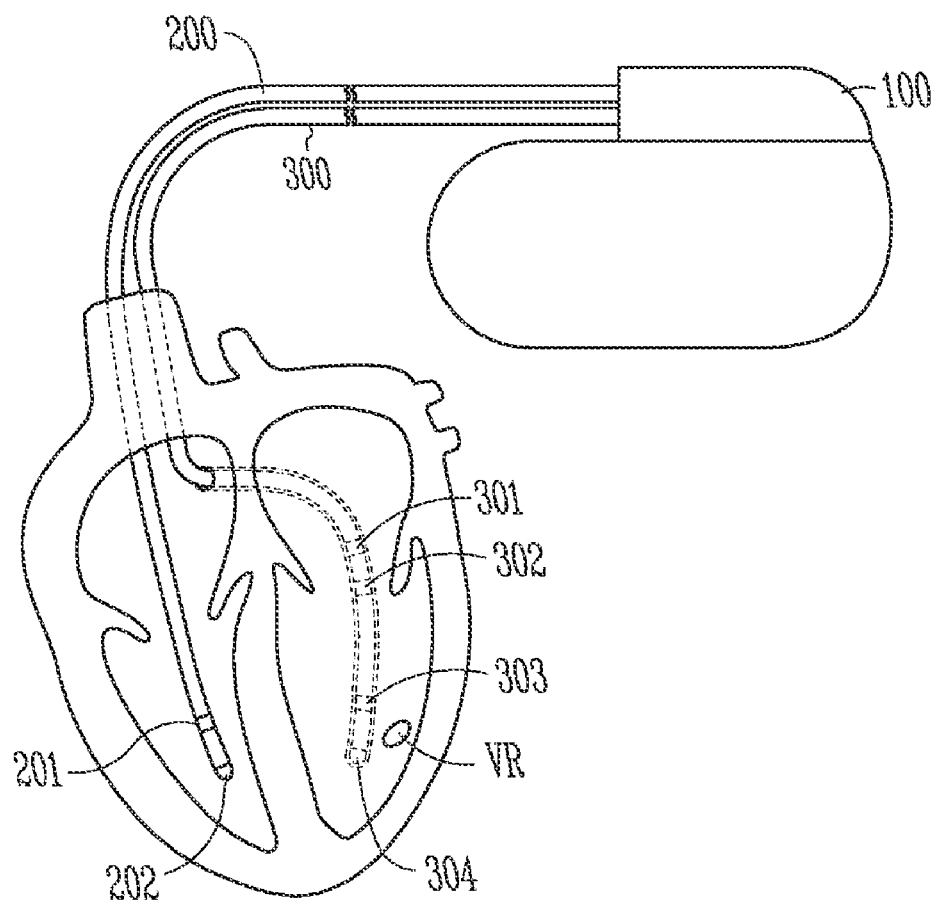
FIG. 1 illustrates the physical configuration of an exemplary pacing device.

Described herein is a method and device for delivering electrical stimulation to the heart in a manner that advantageously redistributes myocardial stress during systole for therapeutic purposes in the treatment of, for example, post-MI and HF patients. Myocardial regions that contract earlier during systole experience less wall stress than later contracting regions. Pacing pulses may be delivered to a particular myocardial region to pre-excite that region relative to other regions during systole, with the latter being excited by intrinsic activation or a subsequent pacing pulse. As compared with an intrinsic contraction, the pre-excited region is mechanically unloaded or de-stressed, while the later excited regions are subjected to increased stress. Such pre-excitation pacing may be applied to deliberately de-stress a particular myocardial region that may be expected to undergo deleterious remodeling, such as the area around a myocardial infarct or a hypertrophying region. Pre-excitation pacing may also be applied to deliberately stress a region remote from the pre-excitation pacing site in order to exert a cardioprotective conditioning effect, similar to the beneficial effects of exercise. Whether for intentionally stressing or de-stressing a myocardial region, pre-excitation pacing may be applied intermittently, either according to a defined schedule or upon detection of specified entry or exit conditions.

Another way to increase myocardial stress is to apply inotropic electrical stimulation to one or more selected myocardial regions. Inotropic electrical stimulation involves delivering voltage pulses to the myocardium in a manner that does not cause a propagating depolarization, termed non-excitatory stimulation, either by reason of being below the excitatory voltage threshold or being delivered during a refractory period of the myocardium. Such inotropic stimulation increases the contractility (i.e., the force of contraction) of the myocardium by increasing intra-cellular calcium concentration and/or by stimulating myocardial sympathetic nerves that release inotropic neurotransmitters. Inotropic stimulation may be applied to the heart to deliberately stress a myocardial region for cardioprotective pre-conditioning and mimic the effects of exercise. As with pre-excitation pacing, inotropic stimulation may be applied intermittently, either according to a defined schedule or upon detection of specified entry and exit conditions.

Pre-excitation pacing may also be combined advantageously with inotropic stimulation. As described above, when pre-excitation pacing is applied to a particular myocardial region, myocardial regions remote from the pre-excited region are excited later during systole than the pre-excited region are subjected to increased stress. If the pre-excitation pacing is applied for the purpose of intentionally stressing the remotely located region(s), inotropic stimulation may also be delivered to the remote region(s) to increase the stress on the region and augment the cardioprotective pre-conditioning effect. If the pre-excitation pacing is delivered for the purpose of mechanically is unloading or de-stressing the pre-excited region, on the other hand, inotropic stimulation may be delivered to the remote region(s) in order to increase the contractility of the remote region and cause a hemodynamically more effective contraction.

Mechanical Effects of Pacing Therapy

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which excitation is conducted from the pacing site to the rest of the myocardium. Regions of the myocardium located more distally from the pacing site are thus excited later than regions proximal to the pacing site as compared with an intrinsic contraction. As explained below, this results in a re-distribution of myocardial wall stress.

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Delivery of a pacing pulse to a ventricular region makes that region contract earlier than other parts of the ventricle. The paced region will therefore be subjected to both a decreased preload and afterload which decreases the mechanical stress experienced by the region relative to other regions during systolic contraction. A region remote from the paced region, on the other hand, will experience increased mechanical stress as it contracts later during systole due to either conduction from the pre-excited site, a subsequent pace applied to the remote region, or intrinsic activation conducted from the AV node.

Applications of Stress Reducing Pre-Excitation Pacing

All but a small fraction of the total amount of oxygen consumed by the myocardium is for the purpose of active muscular contraction during systole, and the oxygen demand of a particular myocardial region increases with increasing systolic wall stress. Causing a particular myocardial region to contract earlier relative to other regions will thus lessen its metabolic demands and the degree of any ischemia that may be present. Particular myocardial regions may also be vulnerable to undergoing deleterious remodeling as a result of increased wall stress in post-MI or HF patients. In order to cause early contraction and lessened stress to a myocardial region vulnerable to becoming ischemic or undergoing remodeling, pre-excitation pacing pulses may be delivered to one or more sites in or around the vulnerable region in a manner that pre-excites those sites relative to the rest of the ventricle and mechanically unloads the vulnerable region. Pre-excitation pacing therapy to unload a vulnerable region may be implemented by pacing the ventricles at a single site in proximity to the vulnerable region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Applications of Stress Augmenting Pre-Excitation Pacing

Another use of pre-excitation pacing is to intentionally stress a region vulnerable to ischemia by pacing at a site(s) remote from the vulnerable region. As described above, such pacing causes increased mechanical stress to the vulnerable region by delaying its contraction during systole relative to other regions. Intermittently stressing a region vulnerable may cause a low level of myocardial ischemia in the region in a patient with demand ischemia, thereby promoting angio-genesis and pre-conditioning the vulnerable region to better withstand the effects of a subsequent ischemic episode. Stress augmentation pacing may also be applied to a weakened region or to a large part of the myocardium in the form of an asynchronous contraction in order to exert a pre-conditioning effect similar to exercise. Pre-excitation pacing therapy to augment stress may be implemented by pacing the ventricles at a single site or multiple sites remote from the region(s) desired to be stressed in accordance with a bradycardia pacing algorithm such as an inhibited demand mode or a triggered mode. Multiple pacing pulses may be delivered to the multiple sites simultaneously or in a defined pulse output sequence.

Applications of Inotropic Stimulation

As described above, inotropic stimulation is non-excitatory electrical stimulation delivered to the myocardium for the purpose of increasing contractility by increasing intracellular calcium concentration and/or stimulation of myocardial nerves. It may be applied in order to cause a hemodynamically effective contraction or to cause increased stress for a pre-conditioning effect that mimics exercise. Inotropic stimulation may be delivered alone or in combination with pre-excitation pacing. In the latter case, inotropic stimulation is most advantageously delivered to the region(s) remotely located from the pre-excitation pacing site in order to either make the ventricular contraction more effective when the pre-excitation pacing is delivered to unload another region or to increase the stress experienced by the remote region when the pre-excitation pacing is delivered for a pre-conditioning effect. Other embodiments include combining intermittent inotropic stimulation with cardiac resynchronization therapy (CRT) or bradycardia pacing. In CRT applications, inotropic stimulation may be triggered or turned on during periods of poor hemodynamic performance or increased demand (e.g., during exercise).

An implantable cardiac rhythm management device such as described below may be configured with lead/electrodes placed on or in the heart (epicardial or endocardial) for the purpose of delivering inotropic stimulation. The device may deliver intermittent inotropic stimulation for short periods of time to the ventricles (e.g., 20 minutes/day, 3 days/week) with the stimulation parameters being fully programmable to meet particular patient requirements. In one form, the inotropic stimulation is programmed to be below the threshold necessary to capture surrounding myocardium but at a level and frequency necessary to capture surrounding myocardial nerves. Since sympathetic innervation of the ventricles is denser than the parasympathetic supply, such regional stimulation will likely cause increased sympathetic activation with resulting positive inotropic effects similar to exercise. Following discontinuation of the inotropic stimulation, intrinsic parasympathetic activation will occur, again similar to exercise. Inotropic stimulation may be delivered synchronously with the cardiac cycle such as multiple or single subthreshold pulses delivered within the ventricular refractory period or outside of the refractory period. Inotropic stimulation pulses may be delivered using pulse generators and leads that provide pacing pulses in addition to non-excitatory inotropic stimulation. The pulse generators may be configured to deliver the inotropic stimulation with a desired amplitude and frequency. For example, inotropic stimulation pulses could be delivered with a pulse width of 10-75 microseconds at a frequency of 1-15 pulses per second. The amplitude may be adjusted to a value so that the stimulation is sub-threshold, where the value will depend upon whether the stimulation is delivered during the refractory period or not. The device may also implement a closed-loop system to monitor heart rate, pressure, flow, contractility, etc. to provide continuous feedback on the inotropic therapy and automatically adjust stimulation parameters if necessary.

Exemplary Implantable Device

FIG. 1 shows an exemplary implantable cardiac device 100 for delivering pre-excitation pacing for the purpose of stressing or de-stressing one or more myocardial regions. The device may also be configured to deliver inotropic stimulation either alone in combination with the pre-excitation pacing. In addition, the device may have the capability of delivering other types of pacing therapy such as bradycardia pacing and cardiac resynchronization pacing. As will be described below, the device may be configured to switch between a normal operating mode and a pre-excitation mode for delivering pre-excitation pacing in accordance with defined entry and exit conditions.

Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to excite or sense right ventricular and/or septal regions, while the electrodes 301-304 are disposed in the coronary sinus or left cardiac veins in order to excite or sense regions of the left ventricle. If a region VR that is vulnerable to remodeling or ischemia were located in the apical region of the left ventricle, pre-excitation pacing to the region could be delivered via electrodes 303 and 304 in a bipolar pacing configuration to de-stress and unload the vulnerable region. Such pre-excitation pacing could be delivered, for example, as left ventricular-only pacing or as biventricular pacing with an offset such that the left ventricle is paced before the right. Conversely, if it were desired to deliberately stress the region VR for cardioprotective pre-conditioning, pre-excitation pacing could be delivered via electrodes 201 and 202 in a right ventricle-only pacing mode or electrodes 301 and 302 in a left ventricle-only or biventricular pacing mode in order to pre-excite a myocardial region remote from the region VR. Inotropic stimulation could be combined with the pre-excitation pacing in either case by delivering inotropic stimulation pulses to a myocardial region remote from the pre-excited region using the electrodes just mentioned or other electrodes. For example, if the pre-excitation pacing were delivered to the region VR via electrodes 303 and 304, inotropic stimulation pulses could be delivered by electrodes 201, 202, 301, and/or 302 during the cardiac refractory period as sensed by those electrodes. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
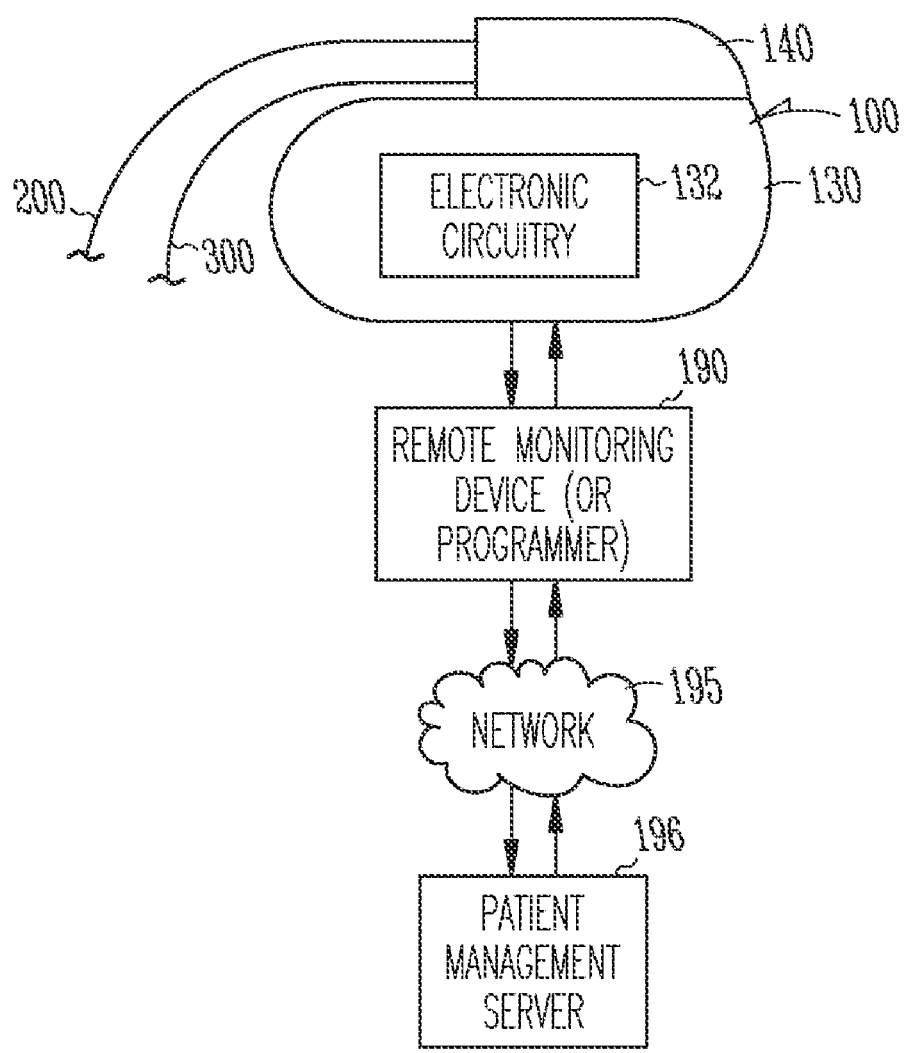
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
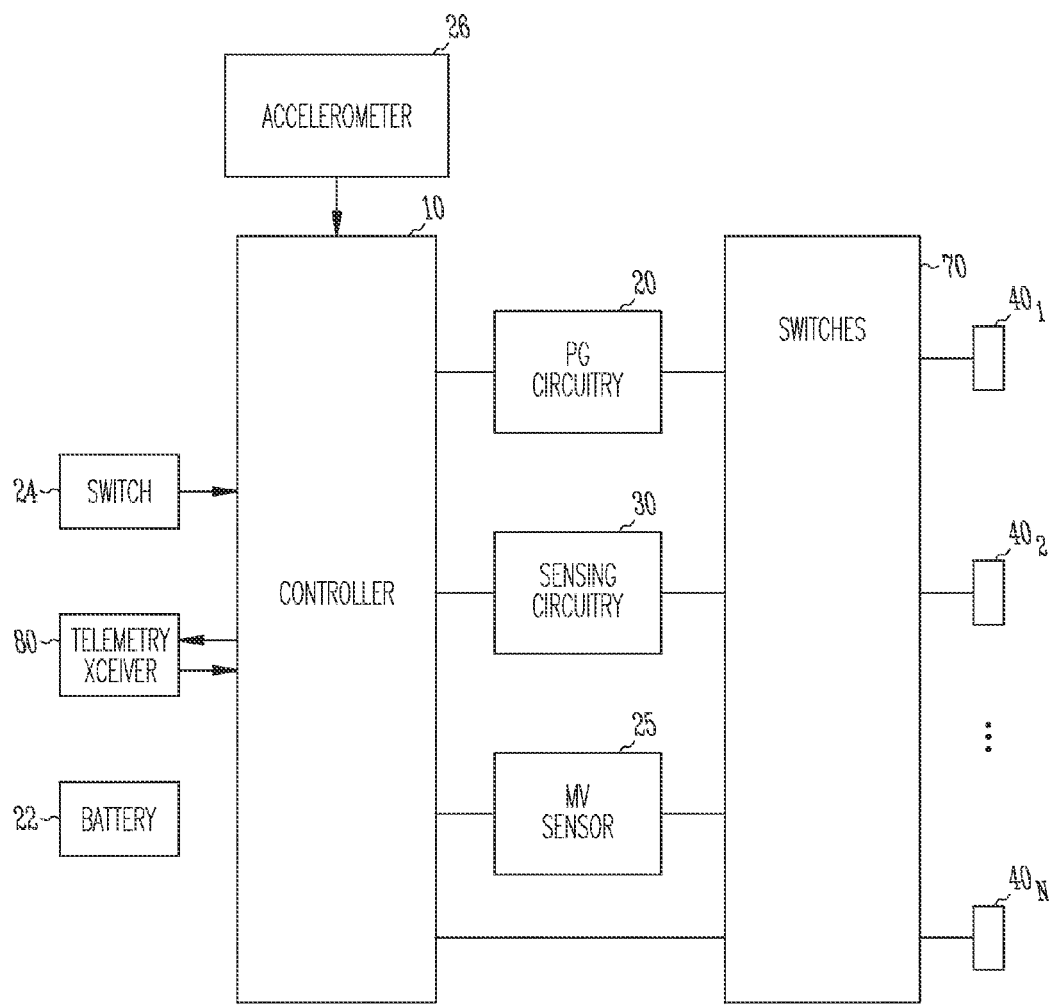
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device. Sensing circuitry 30 and pulse generation circuitry 20 are interfaced to the controller by which the controller interprets sensing signals and controls the delivery of pacing pulses in accordance with a pacing mode (as well as inotropic stimulation pulses). The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse as well as adjustment of pulse energies for the purpose of non-excitatory inotropic stimulation. The pulse generation circuitry may also include a shocking pulse generator for delivering a defibrillation/cardioversion shock via a shock electrode upon detection of a tachyarrhythmia.

Myocardial sites in proximity to an ischemic region may be less excitable than normal and require an increased pacing energy in order to achieve capture. Pacing pulse energies for pre-exciting ischemic regions may be adjusted by programming the device via the telemetry interface in accordance with electrophysiological testing to determine an appropriate pacing pulse energy. The implantable device may also incorporate autocapture, autothreshold, and reconfiguration functionality described in U.S. patent application Ser. No. 11/427,517, filed Jun. 29, 2006, which are especially useful for the delivery of pre-excitation pacing to a vulnerable region because the excitability characteristics of a vulnerable region may change over time. A similar type of function may also be configured to automatically adjust the pulse energies of inotropic stimulation pulses to ensure that they are non-excitatory.

A pacing channel (or an inotropic stimulation channel for delivering inotropic stimulation) is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction/augmentation as well as conventional pacing. The switch matrix allows particular myocardial sites to be pre-excited for purposes of stress reduction or augmentation by selecting the appropriately disposed electrode(s) to be incorporated into a pacing channel used to deliver pre-excitation pacing. Configuration of pacing and sensing channels may be performed via an external programmer communicating through the telemetry interface as well as automatically by the device when switching to or from different pacing modes.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to, or remote from, a vulnerable region may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular or AV interval. The atrio-ventricular interval is triggered by an atrial sense or pace and stopped by a ventricular sense or pace. A ventricular pace is delivered upon expiration of the atrio-ventricular interval if no ventricular sense occurs before the expiration.

In order for pre-excitation pacing to cause early contraction of a paced region relative to other regions located remotely from the pre-excitation site, the latter regions should not be excited until later during systole. In a patient without intact native AV conduction (i.e., an AV block), such later excitation may be accomplished by either spread of the depolarization resulting from pre-excitation to the remote site or application of a subsequent pace if necessary. On the other hand, if native AV conduction is intact and the pre-excitation mode delivers pre-excitation pacing in an atrial tracking or AV sequential pacing mode, the AV delay interval should be selected to be short enough relative to the patient's intrinsic AV interval that the pre-excited site depolarizes well before remotely located regions depolarize due to intrinsic AV conduction. Delivering pre-excitation pacing with a shortened AV interval relative to the patient's intrinsic AV interval (e.g., 30-80% of the intrinsic interval) facilitates pre-excitation by allowing the pre-excitation depolarization to spread beyond the pre-excited site and excite the rest of the myocardium without interference from intrinsic excitation conducted from the AV node. In these cases, the shorter the AV delay interval is relative to the patient's intrinsic AV interval, the more the paced site is pre-excited. In one embodiment, the device is configured to dynamically shorten the AV delay interval in the pre-excitation mode in accordance with a sensed variable that is correlated with the presence of myocardial ischemia such as described above in order to provide more stress reducing pre-excitation as it is needed. For example, the AV delay interval could be shortened in accordance with measured heart rate or exertion level. Shortening the AV delay interval in this manner also compensates for the physiological shortening of the patient's intrinsic AV interval that occurs with increasing heart rate.

Mode Switching

As described above, an implantable pacing device may have the capability of configuring multiple sensing and/or pacing channels using multiple electrodes that can be implanted at selected myocardial sites in the form of unipolar, bipolar, or multipolar leads. The device may then operate in a number of different operating modes, where an operating mode refers to the particular subset of the available electrodes that are configured into sensing and/or pacing channels and the pacing algorithm (i.e., pacing mode) used to determine the timing of the pacing pulses delivered by each pacing channel. If pacing electrodes are disposed at a pre-excitation pacing site(s) in proximity to a selected myocardial region and/or remote from the selected myocardial region, the device may be programmed to operate in a pre-excitation mode that delivers pre-excitation pacing pulses to the selected region in accordance with a programmed pacing mode for the purpose of de-stressing the selected region or for stressing a region(s) located remotely from the pre-excitation pacing site(s). The pre-excitation mode may also include delivery of inotropic stimulation to the remotely located region(s). The device may be programmed to operate in the pre-excitation mode continuously or intermittently. In the latter case, the device may revert to a normal mode when the pre-excitation mode terminates that may include any type of pacing (e.g., bradycardia or cardiac resynchronization pacing) or no pacing at all. Switching to the pre-excitation mode may involve configuring different pacing or sensing channels from those used during the normal mode as well as adjustment of particular pacing parameter such as shortening the AV delay interval used in AV sequential and atrial tracking pacing modes. The device may be configured to switch from the normal mode to the pre-excitation mode in accordance with one or more entry conditions and revert to the normal mode in accordance with one or more exit condition. Entry and exit conditions may also be used to switch between different pre-excitation modes that pre-excite different myocardial regions. For example, one pre-excitation mode may stress a particular region, while another pre-excitation mode may de-stress the same region. Examples of entry and exit conditions include: a lapsed time interval, actuation of a patient-operated switch that the patient may operate, receipt of a telemetry command, detection or non-detection of the presence of myocardial ischemia by the device in accordance with a sensed variable that is correlated with the presence of myocardial ischemia such as features derived from sensed cardiac electrical activity, or a sensed physiological variable being below or above a specified threshold value. The device may be equipped with appropriate sensors and configured to measure physiological variables such as heart rate, minute ventilation, activity level, blood pressure, cardiac output, cardiac impedance, and heart rate variability that can be used for entry and/or exit conditions. A composite entry and/or exit condition may also be formed by ANDing or ORing any of the conditions mentioned above in any desired manner.

Figure 4:
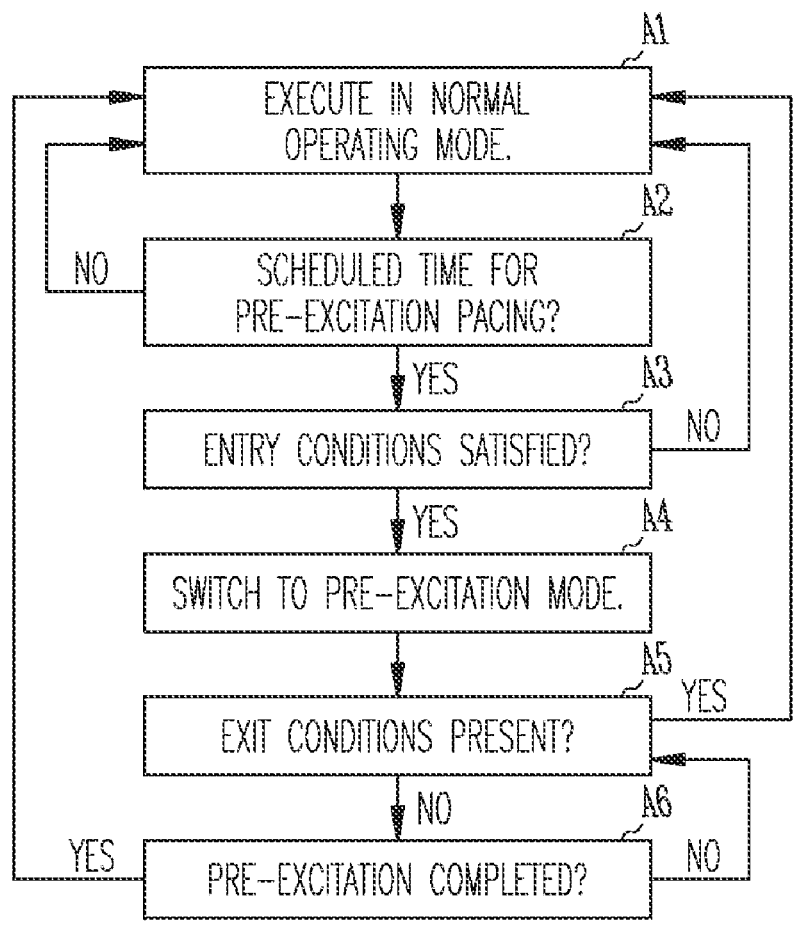
FIG. 4 illustrates an exemplary algorithm for switching between a normal mode and a pre-excitation mode.

FIG. 4 illustrates one way that pre-excitation pacing may be implemented by a cardiac device. In this embodiment, the controller of the device is programmed to transition through a number of different states, designated as A1 through A6. At state A1, the device operates in its normal operating mode. At state A2, while continuing to operate in state A1, the device determines whether it should switch to the pre-excitation mode based upon a lapsed time interval or a triggering condition. Optionally, the device may also be configured to test for one or more particular entry conditions before switching to the pre-excitation mode as implemented by state A3. Examples of entry conditions that must be satisfied before the switch to the pre-excitation mode include a measured exertion level being within a specified entry range, a measured heart rate being within a specified entry range, non-detection of cardiac arrhythmias, non-detection of cardiac ischemia, and actuation of a magnetically or tactilely actuated switch incorporated into the device by the patient that allows delivery of pre-excitation pacing. At state A3, the device checks to see if the one or more entry conditions are satisfied and returns to state A1 if not. If the appropriate entry conditions are satisfied, the device switches to the pre-excitation mode at state A4. The pre-excitation mode supercedes the normal operating mode to the extent necessary to carry out the pre-excitation pacing but may allow certain functions performed in the normal operating mode to continue. Alternatively, the pre-excitation mode could be said to incorporate particular functions of the normal operating mode, which functions are modified if necessary to deliver the pre-excitation pacing. While executing in the pre-excitation mode, the device may optionally be configured to monitor for one or more exit conditions which cause the device to revert to the normal operating mode. Such exit conditions could be the same or different from the entry conditions that must be satisfied before entering the pre-excitation mode. At state A5, while executing in the pre-excitation mode, the device monitors for the occurrence of one or more exit conditions such as a measured exertion level being outside a specified permissible range, a measured heart rate being outside a specified permissible range, presence of a cardiac arrhythmia, presence of cardiac ischemia, and actuation of a magnetically or tactilely actuated switch incorporated into the device by the patient to stop delivery of pre-excitation pacing. If an exit condition occurs, the device returns to the normal operating mode at state A1. Otherwise, the device proceeds to state A6 and checks to see if the prescribed amount and/or duration of pre-excitation pacing has been delivered. If the specified amount or duration of pre-excitation pacing has been delivered, the device returns to state A1 and resumes the normal operating mode. Otherwise, the device loops back to state A5 to monitor for exit conditions.

Inotropic Stimulation

A pre-excitation mode as described above may also include configuration of inotropic stimulation channels that deliver inotropic stimulation pulses to a selected myocardial region (s). Such inotropic stimulation may be delivered as electrical pulses delivered during the refractory period of the stimulated region, sub-threshold pulses delivered at any time during the cardiac cycle, or as high-energy pacing pulses. Inotropic stimulation may be beneficially applied during pre-excitation pacing by inotropically stimulating a region(s) remote from the pre-excited region (i.e., a later excited stressed region). Pre-excitation pacing, whether applied to deliberately stress or de-stress a myocardial region, necessarily results in an asynchronous ventricular contraction that is hemodynamically not as effective as a more synchronous contraction and may result in diminished cardiac output. Inotropic stimulation applied to a stressed region during pre-excitation pacing increases the contractility of the stressed region and may therefore improve the hemodynamics of ventricular contractions during pre-excitation pacing. Also, when pre-excitation pacing is applied to deliberately stress a region for a simulated exercise or cardioprotective effect, inotropic stimulation of the stressed region may be used to further augment the stress introduced by the pre-excitation pacing.

The device may thus be configured so that a pre-excitation mode includes configuration of one or more inotropic stimulation channels that deliver inotropic stimulation to one or more regions remote from the pre-excited region. After implantation of the pacing device and associated leads, the effectiveness of different lead poles (i.e., electrodes) in delivering inotropic stimulation may be determined by hemodynamic testing. The inotropic stimulation channels that result in the greatest improvement in cardiac output may then be used for inotropic stimulation during the pre-excitation mode. Inotropic stimulation channels may also be reconfigured on a periodic basis (e.g., after each or a specified number of cardiac cycles) during the pre-excitation mode to deliver inotropic stimulation to different later-excited and stressed regions. In certain embodiments that utilize multiple pre-excitation modes for delivering pre-excitation pacing to different regions, each such pre-excitation mode may have associated with it one or more particular pacing channels for delivering the pre-excitation pacing as well as one or more particular inotropic stimulation channels for inotropically stimulating a later-excited and stressed region(s).

In most cases, the normal operating mode will result in relatively synchronous ventricular contractions, brought about either by the patient's intrinsic cardiac activity, bradycardia pacing in conjunction with intrinsically conducted excitation, or resynchronization pacing. Inotropic stimulation may still be delivered without accompanying pre-excitation pacing during the normal operating mode for the purpose of improving hemodynamics or for simulating exercise and producing a cardioprotective effect. Such inotropic stimulation may be delivered in manners similar to those discussed above with respect to pre-excitation pacing. For example, specified entry and exit conditions such as discussed above may be used to turn off and turn on the inotropic stimulation during the normal operating mode. Also, the device may periodically rotate between different configurations of inotropic stimulation channels for delivering inotropic stimulation during the normal operating mode. As discussed above, one mechanism by which inotropic stimulation may exert its effects is through stimulation of myocardial sympathetic nerves. For use in either the normal operating mode or a pre-excitation mode, inotropic stimulation channels may be configured with stimulation electrodes implanted in regions of ganglionated plexuses that are mapped using hemodynamics as a feedback indicator. Such regions may include, for example, the superior-basal region of the ventricles (accessible by a coronary sinus lead), the interventricular grooves (accessible by a coronary sinus lead or an endocardial lead), the region adjacent to origin of left obtuse marginal arteries (accessible by a coronary sinus lead), and the interventricular septum (accessible by an endocardial lead).

In an exemplary embodiment, an implantable cardiac device includes a first electrode adapted for disposition near a first myocardial region and a second electrode adapted for disposition near a second myocardial region remote from the first region. The first and second electrodes may be on the same or different leads. The device also includes one or more pulse generators for outputting pacing pulses and a controller programmed to deliver pacing pulses through a pacing channel in accordance with a programmed pacing mode. The controller is programmed to configure the first electrode in a pre-excitation pacing channel and to configure the second electrode in an inotropic stimulation channel. Other electrodes may also be configured into the pre-excitation or inotropic stimulation channel to form bipolar or multipolar pacing configurations. The first or second electrodes, as well as other electrodes, may also be configured into sensing channels for use in delivering the pre-excitation pacing and inotropic stimulation. The controller is then programmed to operate in a pre-excitation mode that includes delivering pre-excitation pacing pulses through the pre-excitation pacing channel in a manner that pre-excites the first myocardial region relative to the second myocardial region and delivering inotropic stimulation to the second myocardial region. The inotropic stimulation may be delivered as multiple non-excitatory pulses delivered during a refractory period of the second myocardial region, as non-excitatory sub-threshold pulses, or as pacing pulses with higher energy than the pre-excitation pacing pulses and delivered subsequently thereto during a cardiac cycle. The controller may also be programmed to intermittently reconfigure the inotropic stimulation and pre-excitation channels with different electrodes. For example, the device may be programmed to intermittently interchange the first and second electrodes in the pre-excitation and inotropic stimulation channels so as to alternately stress and de-stress the first and second myocardial regions. The controller may also be programmed to operate in a normal operating mode and intermittently switch to the pre-excitation pacing mode according to defined entry and exit conditions, where the controller is programmed to deliver no pacing therapy during the normal operating mode, deliver bradycardia pacing therapy during the normal operating mode, or deliver cardiac resynchronization pacing therapy during the normal operating mode. The same or different electrodes used in the pre-excitation mode may be used in the normal operating mode for sensing or delivering therapy. The controller may also be programmed to intermittently deliver inotropic stimulation during the normal operating mode.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. An implantable cardiac device, comprising:
    one or more pulse generators for connecting to electrodes and selectively outputting pacing pulses to an electrode incorporated into a pacing channel or inotropic stimulation to an electrode incorporated into an inotropic stimulation channel;
    a controller programmed to deliver pacing pulses through a pacing channel and inotropic stimulation through an inotropic stimulation channel in accordance with a programmed pacing mode;
    wherein the controller is programmed to configure a first electrode disposed at a first myocardial region in a pre-excitation pacing channel and to configure a second electrode disposed at second myocardial region remotely located from the first myocardial region in an inotropic stimulation channel;
    wherein the controller is programmed to operate in a pre-excitation mode that includes, during a cardiac cycle, delivering pre-excitation pacing pulses through the pre-excitation pacing channel in a manner that pre-excites the first myocardial region relative to the second myocardial region and subsequently delivering inotropic stimulation to the second myocardial region; and,
    wherein the controller is programmed to intermittently interchange the first and second electrodes in the pre-excitation and inotropic stimulation channels so as to alternately stress and de-stress the first and second myocardial regions.

2. The device of claim 1 wherein the controller is programmed to deliver inotropic stimulation as multiple non-excitatory pulses delivered during a refractory period of the remotely located myocardial region.

3. The device of claim 1 wherein the controller is programmed to deliver inotropic stimulation as non-excitatory sub-threshold pulses.

4. The device of claim 1 wherein the controller is programmed to deliver inotropic stimulation as pacing pulses with higher energy than the pre-excitation pacing pulses and delivered subsequently thereto during a cardiac cycle.

5. The device of claim 1 wherein the controller is programmed to intermittently reconfigure the inotropic stimulation and pre-excitation channels with different electrodes after a specified number of cardiac cycles.

6. The device of claim 1 wherein the controller is programmed to operate in a normal operating mode and intermittently switch to the pre-excitation pacing mode according to defined entry and exit conditions.

7. The device of claim 6 wherein the controller is programmed to deliver no pacing therapy during the normal operating mode.

8. The device of claim 6 wherein the controller is programmed to deliver bradycardia pacing therapy during the normal operating mode.

9. The device of claim 6 wherein the controller is programmed to deliver cardiac resynchronization pacing therapy during the normal operating mode.

10. The device of claim 6 wherein the controller is programmed to intermittently deliver inotropic stimulation during the normal operating mode.

11. A method, comprising:
    disposing a first electrode near a first myocardial region;
    disposing a second electrode at second myocardial region remotely located from the first myocardial region;
    configuring the first electrode in a pre-excitation pacing channel and configuring the second electrode in an inotropic stimulation channel;
    operating in a pre-excitation mode that includes, during a cardiac cycle, delivering pre-excitation pacing pulses through the pre-excitation pacing channel in a manner that pre-excites the first myocardial region relative to second myocardial region and subsequently delivering inotropic stimulation to the second myocardial region; and, intermittently interchanging the first and second electrodes in the pre-excitation and inotropic stimulation channels so as to alternately stress and de-stress the first and second myocardial regions.

12. The method of claim 11 wherein the inotropic stimulation is delivered as multiple non-excitatory pulses delivered during a refractory period of the second myocardial region.

13. The method of claim 11 wherein the inotropic stimulation is delivered as non-excitatory sub-threshold pulses.

14. The method of claim 11 wherein the inotropic stimulation is delivered as pacing pulses with higher energy than the pre-excitation pacing pulses and delivered subsequently thereto during a cardiac cycle.

15. The method of claim 11 further comprising intermittently reconfiguring the inotropic stimulation and pre-excitation channels with different electrodes after a specified number of cardiac cycles.

16. The method of claim 11 further comprising operating in a normal operating mode and intermittently switching to the pre-excitation pacing mode according to defined entry and exit conditions.

17. The method of claim 16 wherein no pacing therapy is delivered during the normal operating mode.

18. The method of claim 16 wherein bradycardia pacing therapy is delivered during the normal operating mode.

19. The method of claim 16 wherein cardiac resynchronization pacing therapy is delivered during the normal operating mode.

20. The method of claim 16 further comprising intermittently delivering inotropic stimulation during the normal operating mode.

* * * * *